US006416324B1

(12) United States Patent
Day

(10) Patent No.: US 6,416,324 B1
(45) Date of Patent: Jul. 9, 2002

(54) ONE STEP DENTAL IMPLANT DELIVERY SYSTEM

(75) Inventor: Thomas H. Day, San Diego, CA (US)

(73) Assignee: Sulzer Dental Inc., Carlsbad, CA (US)

( * ) Notice: Subject to any disclaimer, the term of this patent is extended or adjusted under 35 U.S.C. 154(b) by 0 days.

(21) Appl. No.: 09/458,414

(22) Filed: Dec. 10, 1999

(51) Int. Cl.$^7$ ................................................ A61C 8/00
(52) U.S. Cl. ...................................................... 433/173
(58) Field of Search ................................ 432/172, 173, 432/174

(56) References Cited

U.S. PATENT DOCUMENTS

| | | | |
|---|---|---|---|
| 3,990,438 A | 11/1976 | Pritchard | 128/92 |
| 4,027,392 A | 6/1977 | Sawyer et al. | 32/10 |
| 4,177,562 A | 12/1979 | Miller et al. | 133/174 |
| 4,234,309 A | 11/1980 | Sellers | 433/225 |
| 4,259,072 A | 3/1981 | Hirabayashi et al. | 433/173 |
| 4,553,942 A | 11/1985 | Sutter | 433/225 |
| 4,655,711 A | 4/1987 | Weissman | 433/225 |
| 4,712,681 A | 12/1987 | Branemark et al. | 206/438 |
| 4,713,003 A | 12/1987 | Symington et al. | 433/173 |
| 4,758,161 A | 7/1988 | Niznick | 433/173 |
| 4,763,788 A | 8/1988 | Jorneus et al. | 206/438 |
| 4,802,848 A | 2/1989 | Randin | 433/225 |
| 4,856,648 A | 8/1989 | Krueger | 206/63.5 |
| 4,856,994 A | 8/1989 | Lazzara et al. | 433/173 |
| 4,915,629 A | 4/1990 | Sellers | 433/173 |
| 4,927,363 A | 5/1990 | Schneider | 433/173 |
| 4,955,811 A | 9/1990 | Lazzara et al. | 433/173 |
| 4,976,617 A | 12/1990 | Carchidi | 433/141 |
| 4,988,297 A | 1/1991 | Lazzara et al. | 433/173 |
| 4,995,810 A | 2/1991 | Soderberg | 433/141 |
| 5,018,970 A | 5/1991 | Stordahl | 433/75 |
| 5,026,285 A | 6/1991 | Durr et al. | 433/173 |
| 5,030,095 A | 7/1991 | Niznick | 433/173 |
| 5,030,096 A | 7/1991 | Hurson et al. | 433/173 |
| 5,035,619 A | 7/1991 | Daftary | 433/173 |
| 5,062,800 A | 11/1991 | Niznick | 433/229 |
| 5,073,111 A | 12/1991 | Daftary | 433/173 |
| 5,076,788 A | 12/1991 | Niznick | 433/173 |
| 5,100,323 A | 3/1992 | Friedman et al. | 433/173 |
| 5,106,300 A | 4/1992 | Voitik | 433/173 |
| 5,108,288 A | 4/1992 | Perry | 433/173 |
| 5,125,840 A | 6/1992 | Durr et al. | 433/173 |
| 5,145,372 A | 9/1992 | Daftary et al. | 433/173 |
| 5,167,664 A | 12/1992 | Hodorek | 606/73 |
| 5,180,303 A | 1/1993 | Hornburg et al. | 433/173 |
| 5,197,881 A | 3/1993 | Chalifoux | 433/173 |
| 5,209,659 A | 5/1993 | Friedman et al. | 433/173 |
| 5,281,140 A | 1/1994 | Niznick | 433/172 |
| 5,282,746 A | 2/1994 | Sellers et al. | 433/172 |
| 5,297,963 A | 3/1994 | Dafatry | 433/172 |

(List continued on next page.)

FOREIGN PATENT DOCUMENTS

SU          001727808 A1       4/1992

OTHER PUBLICATIONS

Spline Dental Implant System Technical Products Addendum, Cat. No. 4717, 6/96, pp. SP-15 and SP-16.

Primary Examiner—Nicholas D. Lucchesi
(74) Attorney, Agent, or Firm—Philip S. Lyren

(57) ABSTRACT

A dental implant healing screw formed from two pieces: a threaded shaft and a collar. The healing screw functions as a conventional healing cap to protect the coronal end of the dental implant and as a driver to drive the dental implant during the implantation procedure.

24 Claims, 14 Drawing Sheets

U.S. PATENT DOCUMENTS

| | | | |
|---|---|---|---|
| 5,312,254 A | 5/1994 | Rosenlicht | 433/173 |
| 5,316,476 A | 5/1994 | Krauser | 433/173 |
| 5,322,443 A | 6/1994 | Beaty | 433/141 |
| 5,336,090 A | 8/1994 | Wilson, Jr. et al. | 433/172 |
| 5,338,196 A | 8/1994 | Beaty et al. | 433/172 |
| 5,362,235 A | 11/1994 | Daftary | 433/172 |
| 5,366,374 A | 11/1994 | Vlassis | 433/165 |
| 5,368,160 A | 11/1994 | Leuschen et al. | 206/339 |
| 5,415,545 A | 5/1995 | Shaw | 433/173 |
| 5,431,567 A | 7/1995 | Daftary | 433/172 |
| 5,437,550 A | 8/1995 | Beaty et al. | 433/141 |
| 5,437,551 A | 8/1995 | Chalifoux | 433/173 |
| 5,449,291 A | 9/1995 | Lueschen et al. | 433/173 |
| 5,468,150 A | 11/1995 | Brammann | 433/173 |
| 5,482,463 A | 1/1996 | Wilson, Jr. et al. | 433/173 |
| 5,484,285 A | 1/1996 | Morgan et al. | 433/173 |
| 5,527,182 A * | 6/1996 | Willoughby | 433/173 X |
| 5,538,428 A | 7/1996 | Staubli | 433/173 |
| 5,580,246 A | 12/1996 | Fried et al. | 433/172 |
| 5,582,299 A | 12/1996 | Lazzara et al. | 206/63.5 |
| 5,622,500 A | 4/1997 | Niznick | 433/173 |
| 5,630,717 A | 5/1997 | Zuest et al. | 433/172 |
| 5,704,788 A | 1/1998 | Milne | 433/173 |
| 5,733,123 A | 3/1998 | Blacklock et al. | 433/173 |
| 5,755,575 A | 5/1998 | Biggs | 433/173 |
| 5,897,319 A | 4/1999 | Wagner et al. | 433/174 |
| 6,168,436 B1 * | 1/2001 | O'Brien | 433/173 |

* cited by examiner

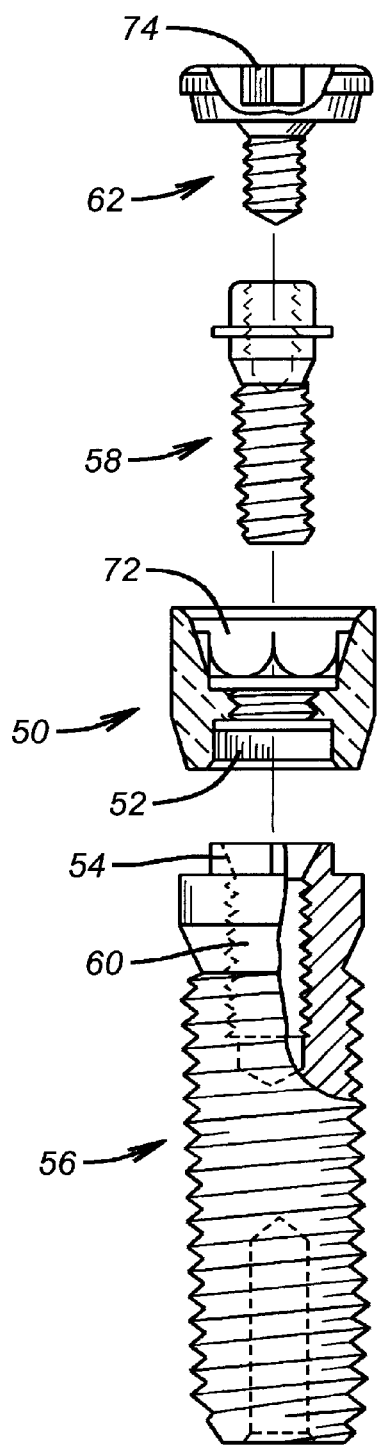
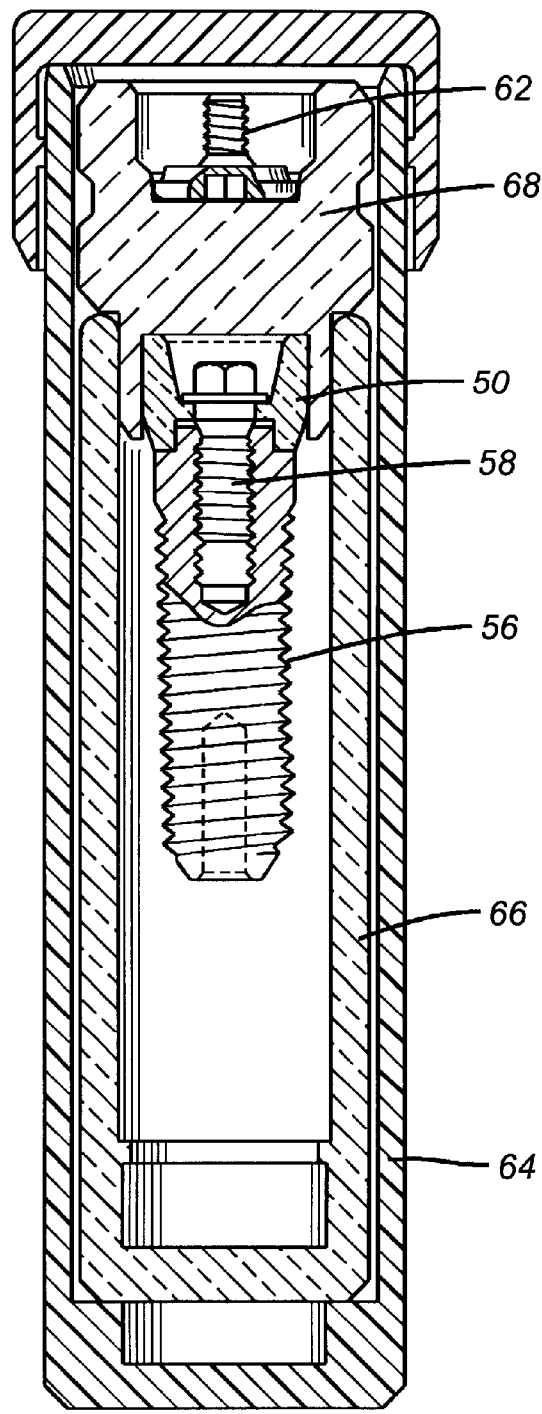
(PRIOR ART)
FIG. 1B
(PRIOR ART)
FIG. 1C

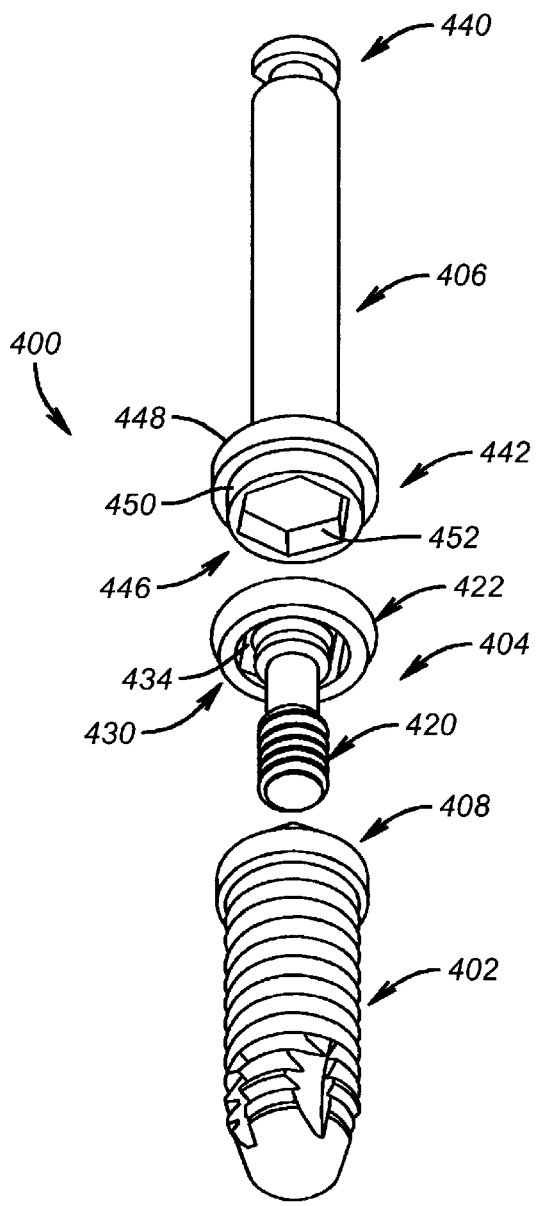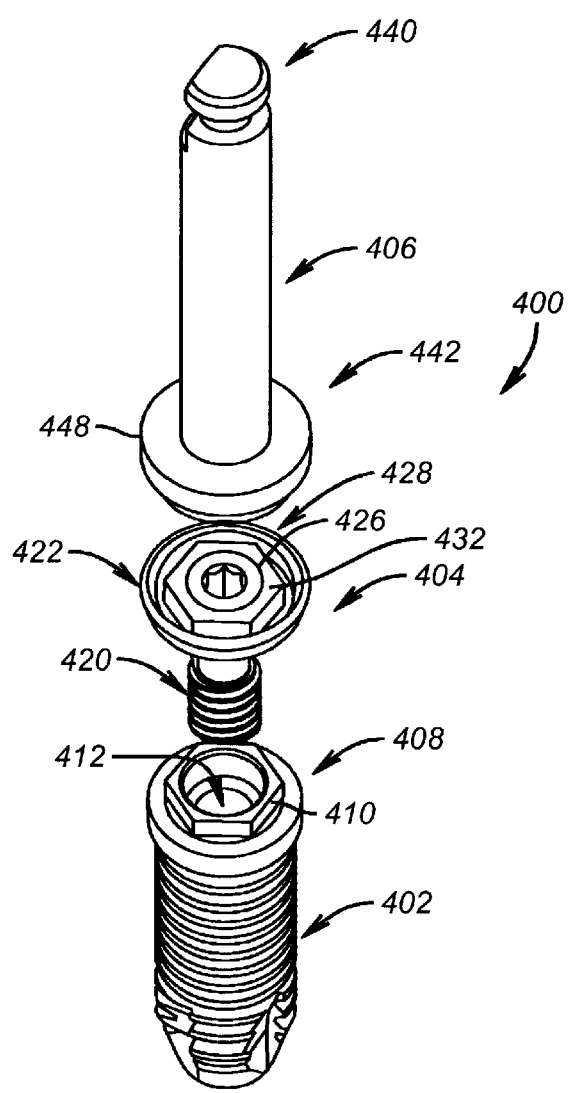
FIG. 11A   FIG. 11B

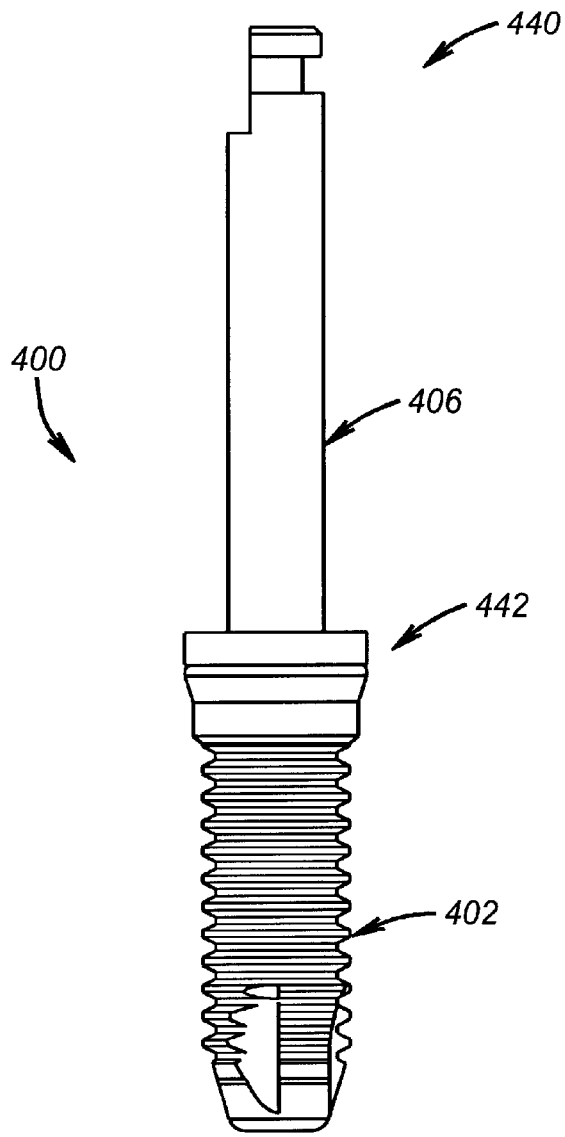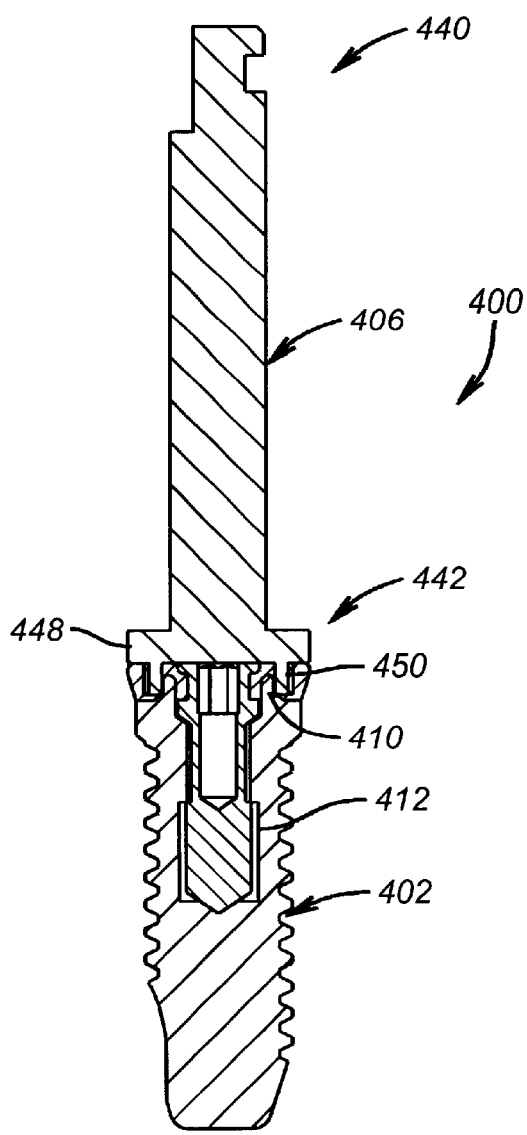
FIG. 12A   FIG. 12B

ONE STEP DENTAL IMPLANT DELIVERY SYSTEM

FIELD OF THE INVENTION

The present invention relates generally to dental implants, and particularly to a dental implant delivery system and method for using the system.

BACKGROUND OF THE INVENTION

Dental implants are typically packaged and shipped in a package that includes an implant delivery system. The implant delivery system is maintained in a sterile environment and is opened just before the implant is needed during the surgical implantation procedure.

FIG. 1A illustrates an example of one such prior dental delivery system shown generally at 10. Delivery system 10 includes a vial 12 housing a threaded implant 14 and a driver mount 16.

The vial (shown as a partial cross-sectional view) has an elongated cylindrical configuration forming an internal cavity with a shoulder 13. The vial is used to transport the implant and driver mount. A lid (not shown) fits on top of the vial to seal and retain the implant and driver mount.

Implant 14 is shown having an external threaded section 18 and a top coronal section 20. The coronal section includes a hexagonal projection 22 for mating with different dental components, such as a dental abutment.

The driver mount includes a bottom portion having a hexagonal recess 24 that engages with the hexagonal projection 22 on the implant. The driver mount also includes a bottom portion, a top portion, and a flange 26 extending outwardly between these two portions. This flange has a disc shape and has a larger diameter than the bottom portion.

A screw 28 secures the driver mount to the implant. Once connected, the driver mount and implant together fit within the internal cylindrical cavity formed within the vial. The flange 26 rests on the internal shoulder 13 to hold the implant and the driver mount in the vial and keep the implant from touching the sides or bottom of the vial.

In order to install implant 14 into a patient's jawbone, an implant site is prepared using conventional surgical procedures. Typically, an incision is made along the gingival tissue at the implant site, and a cylindrical bore is drilled into the jawbone. Once the drilling steps are finished and the site is fully prepared, the implant is ready to be inserted into the jawbone. First, a wrench, such as a motorized dental handpiece, is fitted with a driving tool and then to the end of the driver mount. Typically the driving tool functions as an adapter between the wrench and the driver mount attached to the top of the implant. The driving tool is then used to remove the implant and driver mount from the vial. The end of the implant is fit within the bore of the jawbone, and the drive tool drives the implant into position within the bone. Once the implant is driven to the desired depth, the driving tool is removed from the end of the driver mount. Then, the screw 28 holding the driver mount is removed from the implant. If the implant has been placed in soft bone, the torque used to remove the driver mount screw may also act to unscrew the entire driver mount-implant assembly. In these cases, a countertorque tool is fitted to the driver mount to prevent the driver mount from rotating as the driver mount screw is removed. Now, the driver mount can be detached from the end of the implant. Once the driver mount is removed, the coronal end of the implant is exposed and must be covered. A separate healing cap (not shown) is obtained and positioned at the coronal end of the implant. A tool, different from that used to drive the implant, is used to screw the healing cap to the implant. The gingival tissue is then sutured, and the implant remains within the bone for several months as osseointegration and healing occur. During a second surgical procedure, the implant is re-exposed, the healing cap is removed, and a dental prosthesis is affixed to the implant.

FIGS. 1B and 1C show a prior art dental implant delivery system taught in U.S. Pat. No. 5,622,500 entitled "Insertion Tool/Healing Collar/Abutment." A healing collar 50 has an opening 52 that engages a male projection 54 of dental implant 56. A screw 58 passes through the healing collar and threads into an internal cavity 60 to connect the healing collar to the implant. A separate cover screw 62 screws into the top of the screw 58. The implant, healing collar, and screws are packaged in a cylindrical container 64 that surrounds a vial 66. A stopper 68 fits on top of the vial and holds the implant and healing collar at one end and the cover screw at an opposite end.

In order to place the implant, the stopper 68 is removed from the vial 66 and transported to the implant site. The distal end of the implant is positioned into the bore in the jawbone until the stopper frictionally disengages from the healing collar. Then, a driving tool (not shown) is inserted into an opening 72 of the healing collar in order to drive the implant into the jawbone. The driving tool is removed, and the cover screw 62 is positioned onto the top of screw 58. Another dental driving tool is then inserted into a passage 74 of the cover screw to screw it into the screw 58.

Prior dental implant delivery systems have numerous disadvantages. One important disadvantage is that numerous surgical steps are required to implant a dental implant. As discussed above, these steps include uninstalling a driver mount, installing a healing cap, and changing driving tools several times. If many of these steps could be eliminated, the surgical implantation procedure would be much simpler, quicker, easier to learn, safer, and ultimately more efficient.

Another disadvantage is that prior delivery systems require various different tools and components to implant the dental implant. For example, a separate driver mount and driver mount screw are connected to the implant. Then, a driving tool connects to the driver mount to drive the implant into the bone. A countertorque tool and driver mount screw removal tool are then used to remove the driver mount and its screw. Next, a separate healing cap and accompanying healing screw are placed on the end of the implant. Yet another driving tool is then used to tighten the healing cap. If many of these tools and components were eliminated, fewer parts would be required to install an implant; and a significant cost savings could be realized.

Another disadvantage is that during the implantation procedure, the internal cavity of the implant may be susceptible to bacteria or other foreign material. Once the implant is driven into the jawbone, the driver mount is removed, and the internal cavity of the implant is exposed until the healing cap is positioned over this cavity. During the time before the healing cap is in place, bacteria or other foreign material may get inside the internal cavity of the implant. These trapped contaminants may increase the probability of infection, or solidify during the healing screw process, forming an adhesive glue inside the implant. This glue can make the healing cap difficult to remove during subsequent procedures. Elimination or reduction of this occurrence would provide benefits to the patient and doctor.

Another disadvantage is that the driver mount may add unwanted length or width to the delivery system. For example, some driver mounts (like the one shown in FIG. 1) are wider than the implant. In some instances then, it may be difficult or impossible to completely position the wide driver mount within tight inter-dental spaces. In particular, during a single tooth restoration, the implant often must be driven between two adjacent teeth, and the distance between these teeth may be too narrow to accommodate the driver mount. As another example, prior driver mounts add additional length to the end of the driving tool/driver mount/implant assembly. This additional length may make it difficult or impossible to properly position and then drive the implant into the bone. In particular, some locations in the posterior mandible or maxilla cannot be accessed if the implant, driver mount, and driving tool form an overall length that is too long.

As another disadvantage, the driver mount can occlude the view of the anti-rotational feature on the end of the implant. Most dental implants have an anti-rotational feature (such as a hexagon, octagon, or plurality of tines) at the coronal end that engages with a corresponding dental component, like an abutment. During some implantation procedures (for example, installation in the anterior mandible or maxilla), the doctor may need to view the orientation of these anti-rotational features once the implant is seated to the proper depth in the jawbone. In order to obtain this view, the driver mount must first be removed. If the implant is not correctly oriented, then the driver mount must be re-installed and the implant rotated to the correct position.

The present invention solves the problems discussed with prior dental delivery systems and provides further advantages.

SUMMARY OF THE INVENTION

The present invention is directed toward a dental implant delivery system that includes a dental implant, a driving tool, and a healing screw. The healing screw both drives the implant into the jawbone during implantation and protects the coronal end of the implant during osseointegration. The dental implant may be installed in the jawbone of the patient with a greatly reduced number of surgical steps and tools.

The dental implant includes a distal end, a threaded section, and a coronal end. The coronal end includes an engaging feature (such as a hexagon or Spline tines) and a threaded bore extending into the body of the implant.

The driving tool includes two ends. One end connects to a dental wrench (such as a motorized dental handpiece), and the other end connects to and engages with the healing screw.

The healing screw includes a separate shaft and collar. The shaft has external threads at one end to threadably engage the threaded bore of the implant. The other end of the shaft connects to the collar and has a bore extending into the body of the shaft. The collar fits around the shaft and includes two engaging regions: one region engages the driving tool, and the other region engages the engaging feature at the coronal end of the implant. In the preferred embodiment, the shaft is able to rotate while connected to the collar. As such, the collar can be engaged with the engaging feature of the implant while the shaft is threaded into the threaded bore of the implant, thus seating the healing screw on the implant.

The delivery system of the present invention is particularly advantageous because the number of steps required to implant a dental implant is very small. The delivery system does not include a separate driver mount since the healing screw functions to drive the implant. As such, no steps are required to install or remove a separate driver mount or like component. Further, the healing screw also functions to protect and cover the coronal end of the dental implant. The healing screw is connected to the coronal end of the implant by the manufacturer. As such, a separate healing cap does not have to be installed on the coronal end of the dental implant during the implantation procedure. Further yet, one single tool is required to install the implant into the jawbone. Separate tools for driving the implant, removing the driver mount screw, holding the driver mount with removing the driver mount screw, and installing the healing cap are not required. Further yet, the risk of contaminating the implant or dropping one of the dental components is greatly reduced since the number of surgical steps and number of components are minimized.

The following summary briefly describes the method using the implant delivery system of the present invention and illustrates the small number of surgical steps required to implant a dental implant: During the implantation procedure, the implantation site is prepared using conventional techniques. Once the site is prepared, the dental implant and connected healing screw are obtained. The driving tool engages the tool engaging region of the healing screw, and the dental implant is moved to the implantation site. Once at the implantation site, the driving tool drives the implant and healing screw into the jawbone. The healing screw functions as a driver mount while the implant is driven into the bone. In this regard, the healing screw transfers torque from the driving tool to the implant. After the implant is fully seated in the jawbone, the driving tool is disengaged from the healing screw. The healing screw is left on the coronal end of the implant. Now the healing screw functions as a conventional healing cap and protects the coronal end of the implant. At this point, the implantation procedure is complete, and the implantation site can be closed using conventional techniques.

As another advantage, once the implant is driven to the desired location, no components (such as a driver mount or conventional healing cap) need to be removed from or added to the implant. The healing-screw of the present invention is connected to the dental implant by the manufacturing during packaging. As such, movement and disturbance of the implant are minimized. With the delivery system of the present invention, once the implant is driven to the correct position and orientation, the healing screw serves as the noted healing cap. Typically, this healing screw will not be removed until sometime later when the dental prosthesis is ready to be attached to the implant.

As another advantage, various different tools are not required to implant the dental implant of the present invention. In the present delivery system, a single driving tool is needed to implant the implant. The driving tool engages the tool engaging region of the healing screw to carry or transport the implant to the implantation site. Then, the same driving tool (while still connected to the healing screw) drives the implant into the jawbone. Once the implant is positioned into the jawbone, the driving tool is removed. No other tools are required to install the implant.

As another advantage, the internal cavity of the implant is continuously covered and thus less susceptible to bacteria or other foreign material. The healing screw of the present invention is placed on the coronal end of the implant during packaging. During the implantation procedure, the implant is removed from the packaging, and the implant is positioned into the jawbone. The healing screw is not removed during these surgical steps and, thus, continuously helps to seal and protect the coronal end of the implant.

As another advantage, the delivery system of the present invention does not include a separate driver mount that adds unwanted length or width to the delivery system. The healing screw fits snugly on the implant and adds a very small amount of additional height to the coronal end. Further, the healing screw is sized to have about the same diameter as the implant, so no additional width is added. The implant delivery system of the present invention thus can be used in instances when access to the restoration site is narrow or limited in space or when the interdental space is very small or narrow.

As another advantage, the view of the anti-rotational feature on the end of the implant is not occluded. While the healing screw is positioned on the end of the implant, the anti-rotational features are visible. As such, no components (such as a driver mount or healing cap) need to be removed during the implantation procedure to view the orientation of the anti-rotational features.

As yet another advantage, the implant procedure minimizes the amount of handling or contact with the components of the implant delivery system and other tools. As such, the likelihood that a component may be dropped, mishandled, contaminated, or otherwise misplaced is greatly reduced.

As another advantage, fewer steps are required to place the implant. This reduces the time required for surgery. This time increases the profitability of the surgical procedure for the surgeon, and also reduces discomfort to the patient. The reduced number of steps also makes the surgical procedure easier to learn and remember. This is beneficial to the inexperienced surgeon or someone who places dental implants infrequently.

As another advantage, the number of disposable parts supplied with each implant is reduced. The healing screw of the present invention replaces a driver mount, driver mount screw, and healing cap. This results in substantial cost savings.

As another advantage, a reduced and more consistent healing screw removal torque is achieved. Preferred embodiments of the healing screw require a small frictional engagement between the collar and shaft. This frictional engagement greatly reduces the probability of spontaneous screw loosening of the healing screw during the healing period, which can endure for several months. The two-piece design of the healing screw also prevents loads on the collar from being directly transferred as loosening torque to the threaded shaft. The reduced probability of healing screw loosening allows a reduced initial tightening torque to be used. This initial lower torque is can also be more consistent as it is applied by the manufacturer during packaging under controlled conditions and using precision torque tightening equipment.

As yet another advantage, the position of the implant can be easily adjusted at any time during placement. Prior art healing caps are typically made of the same material as the implant itself. Once a prior art healing cap has been attached to the implant, neither the orientation of the implant's anti-rotational features nor the vertical position of the implant's abutment mounting surface can be easily discerned. In contrast, the preferred embodiments of the invention utilize a different, visually contrasting material for the collar of the healing screw than for the implant. This allows easily visual identification of the critical implant-to-abutment interface. The surgeon can identify both the angular orientation and the vertical height of the implant at all times, and can adjust both at any time without removing a typical healing cap or remounting any kind of typical driver mount.

The invention, accordingly, comprises the apparatus and method possessing the construction, combination of elements, and arrangement of parts that are exemplified in the following detailed description. For a fuller understanding of the nature and objects of the invention, reference should be made to the following detailed description taken in connection with the accompanying drawings.

BRIEF DESCRIPTION OF THE DRAWINGS

The invention will hereafter be described with reference to the accompanying drawings, wherein like reference numerals denote like elements, and:

FIG. 1B is a view of a prior art dental implant and healing collar.

FIG. 1C is the implant and healing collar of FIG. 1B in an implant package.

FIG. 11A is an exploded perspective view of an alternate embodiment the dental implant delivery system of the present invention.

FIG. 11B is another exploded perspective view of FIG. 11A.

FIG. 12A is a plan view of FIG. 11A of the driving tool and healing screw connected to the dental implant.

FIG. 12B is a cross sectional view of FIG. 12A.

DESCRIPTION OF THE PREFERRED EMBODIMENTS

Figure 1A:
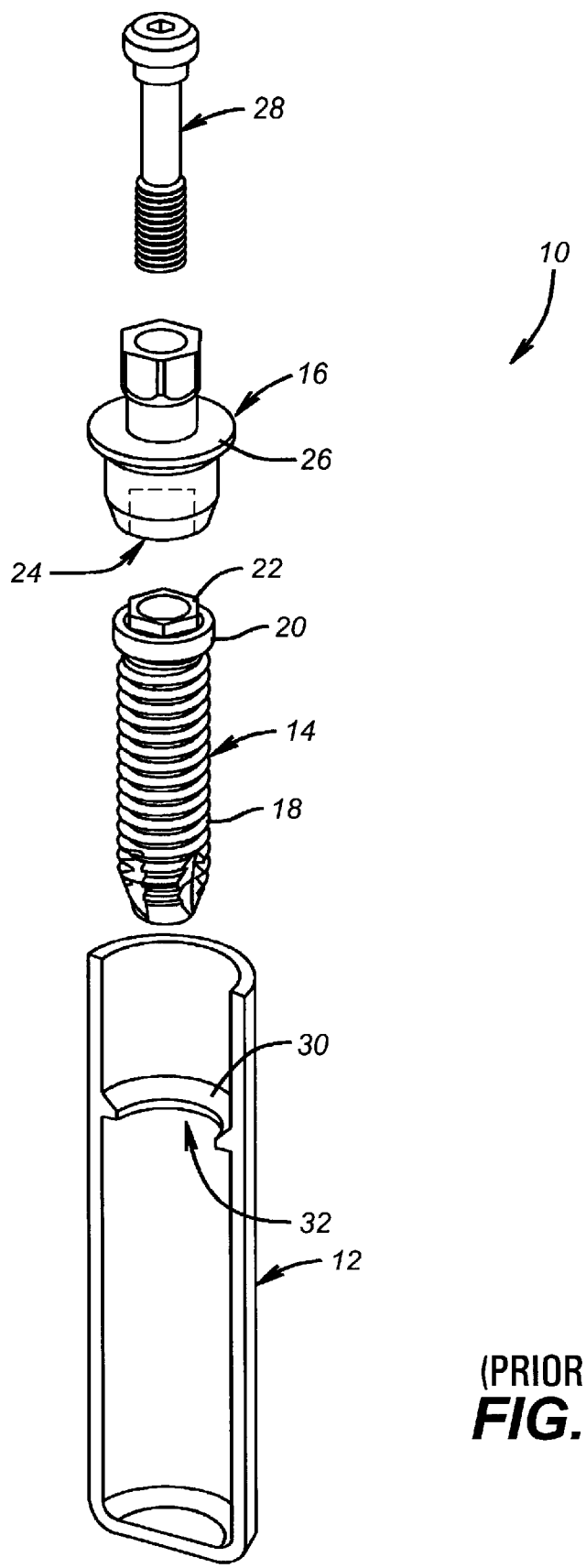
FIG. 1A is a perspective view of a prior art dental implant delivery system.
Figure 2:
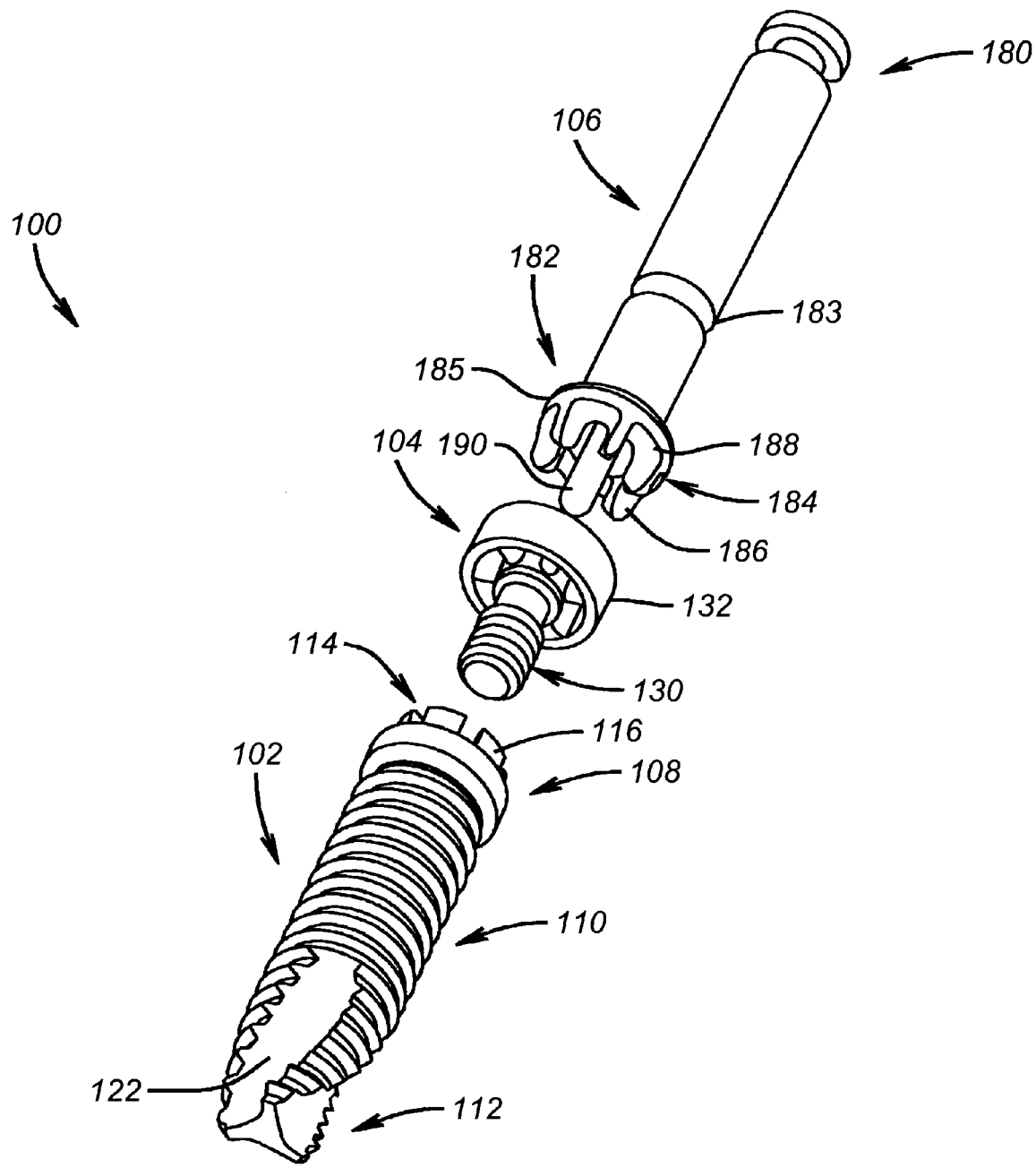
FIG. 2 is an exploded perspective view of the dental implant delivery system of the present invention.
Figure 3:
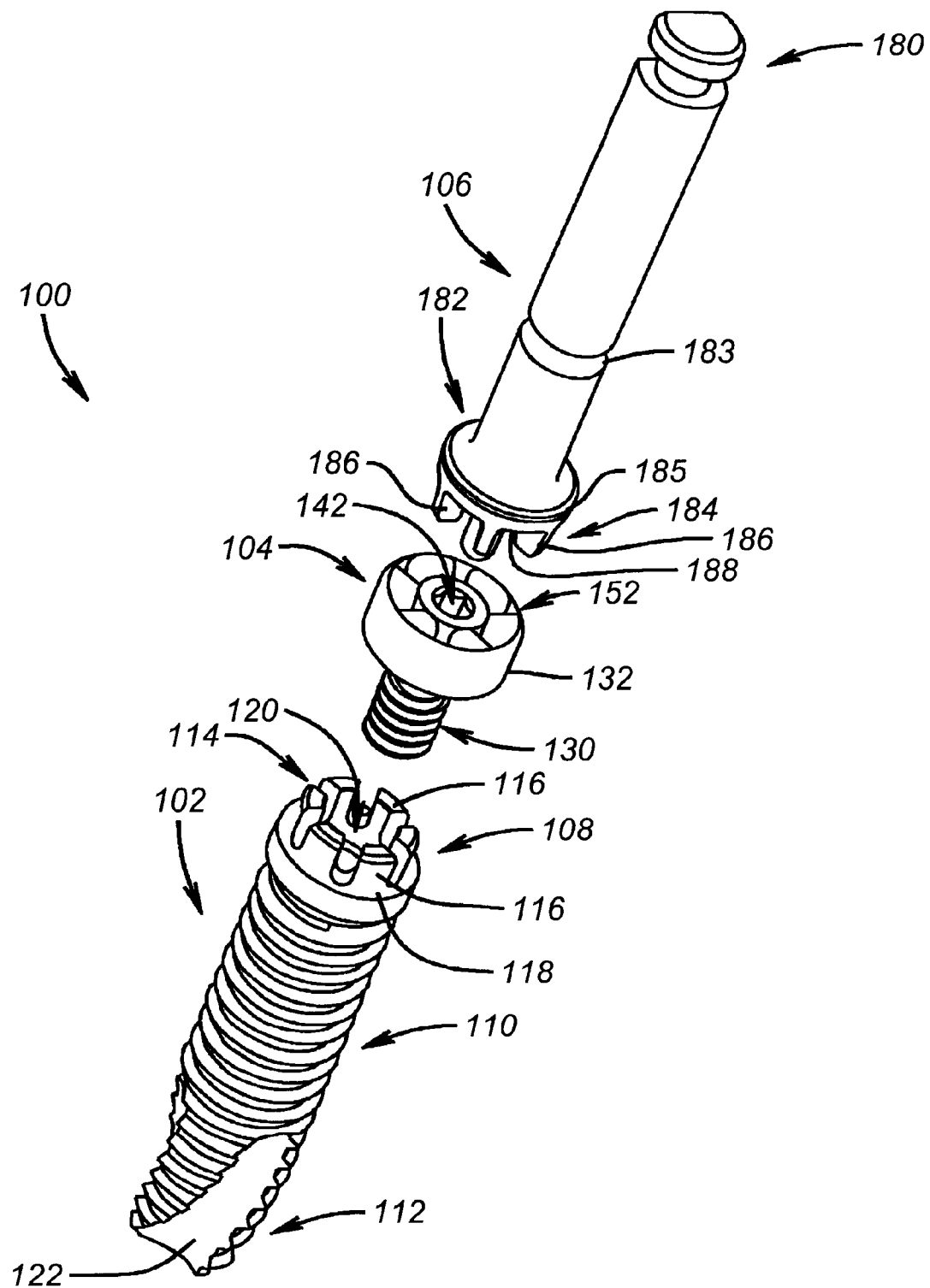
FIG. 3 is another exploded perspective view of the dental implant delivery system.

FIGS. 2 and 3 show a dental implant delivery system 100 according to a preferred embodiment of the present invention. The delivery system generally includes a dental implant 102, a healing screw 104, and a driving tool 106.

The implant 102 may be any one of various implants known to those skilled in the art, such as a TWIST™ implant manufactured by Sulzer Calcitek Inc. of Carlsbad, Calif. Generally, implant 102 includes a coronal end 108, a body portion 110, and a distal end 112. The coronal end has an engaging feature 114 having a plurality of male tines 116 extending upwardly from an end surface 118. Coronal end 108 also includes a threaded axial bore 120 extending downwardly into the body 110 of the implant. The body portion has external threads, and the distal end 112 has a plurality of self-tapping features 122.

Looking also to FIGS. 4A–4E, healing screw 104 consists of two separate and distinct components: a shaft 130 and a collar 132. The shaft 130 has an elongated cylindrical configuration with a proximal end 134 and a distal end 136. The proximal end has a lip 138 that extends outwardly and circumferentially from a smooth cylindrical body portion 140. The proximal end also includes an axial bore 142 having an engaging surface 144. This engaging surface has a polygonal shape (such as a hexagon) for engaging a dental tool to tighten or loosen the healing screw to the implant. The distal end 136 includes a threaded exterior for threadably engaging with the threaded axial bore 120 of the implant 102.

The collar 132 has a ring or cylindrical shape with a central opening 150 extending through its body. The collar has two engaging regions. One engaging region 152 (seen best in FIG. 4D) is located at a proximal end 154; and another engaging region 156 (seen best in FIG. 4C) is located at a distal end 158. Engaging region 152 is designed to engage the end of driving tool 106 and has a plurality of cavities or recesses 160. Engaging region 156 is designed to engage the engaging feature 114 of implant 102 and has a plurality of cavities or recesses 162. These cavities 162 are shaped to receive and engage male tines 116 of implant 102.

Figure 4A:
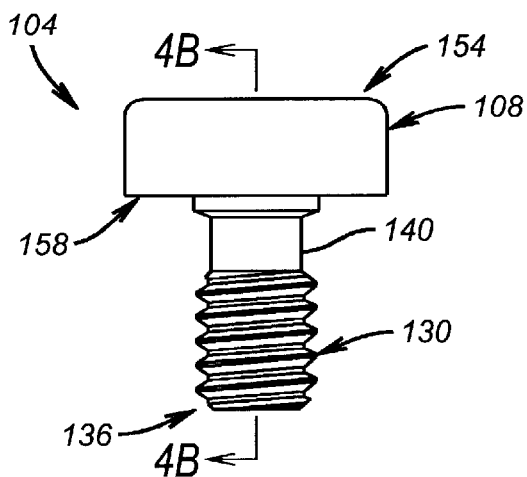
FIG. 4A is a plan view of the healing screw.
Figure 4B:
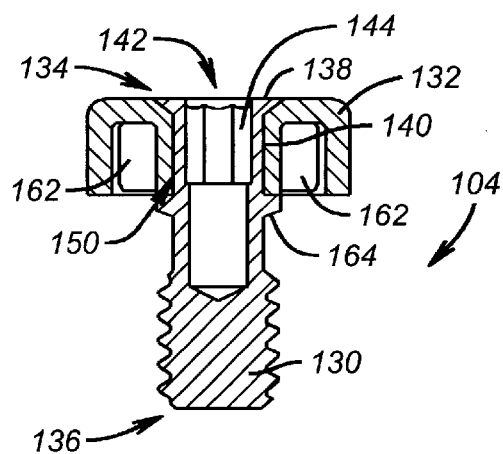
FIG. 4B is a cross sectional view taken along line 4B of FIG. 4A.
Figure 4C:
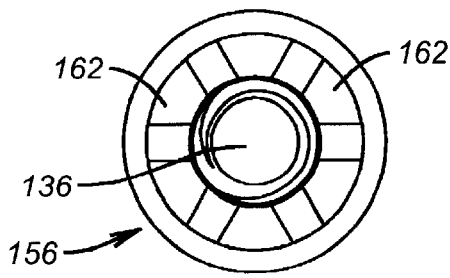
FIG. 4C is a bottom view of the healing screw of FIG. 4A.
Figure 4D:
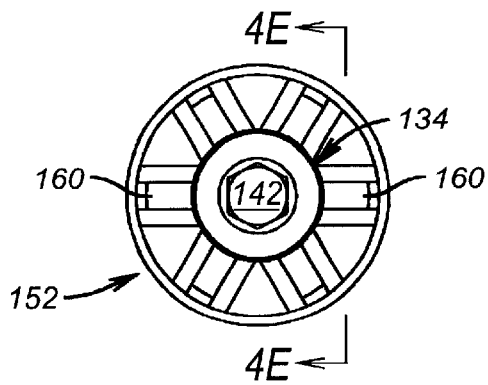
FIG. 4D is a top view of the healing screw of FIG. 4A.
Figure 4E:
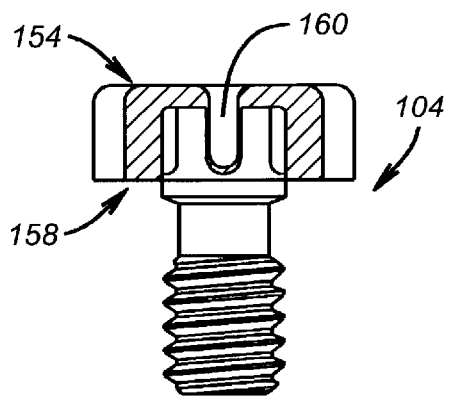
FIG. 4E is a cross section view taken along the line 4E of FIG. 4D.

The cavities 160 extend downwardly toward the distal end 158, while the cavities 162 extend upwardly toward the proximal end 154. Preferably, neither of these cavities forms an opening completely through the collar; instead both remain imperforate. As such, bacteria or other foreign material cannot migrate through the cavities. Further, the cavities may have a variety of shapes, such as rectangular, square, triangular, circular, oval, or other polygonal shapes. Further yet, the number of cavities may vary. FIG. 4D, for example, shows six cavities, while FIGS. 11A and 11B (discussed below) show one cavity.

The central opening 150 of the collar is sized to receive and snugly fit around the smooth body portion 140 of the shaft. Preferably, the collar is not removable from the shaft once around this body portion. In this regard, the lip 138 prevents the collar from moving off the proximal end of the shaft. The shaft also includes a shoulder 164 that extends circumferentially around the body portion 140. This shoulder 164 prevents the collar from moving toward the distal end of the shaft.

Preferably, the shaft is made from biocompatible metal (such as titanium); and the collar is made from biocompatible thermoplastic polymer (such as polyaryletherketone). The collar may be injection molded around proximal end of the shaft to fit between the lip 138 and the shoulder 164.

Figure 5A:
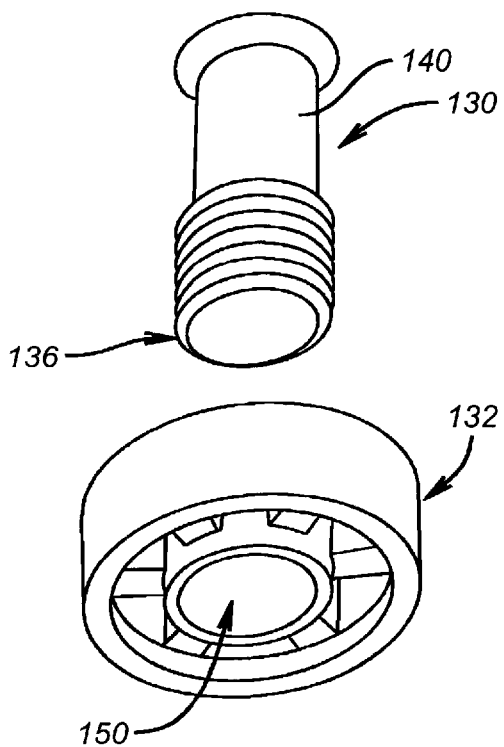
FIG. 5A is an exploded perspective view of an alternate embodiment of the healing screw.
Figure 5B:
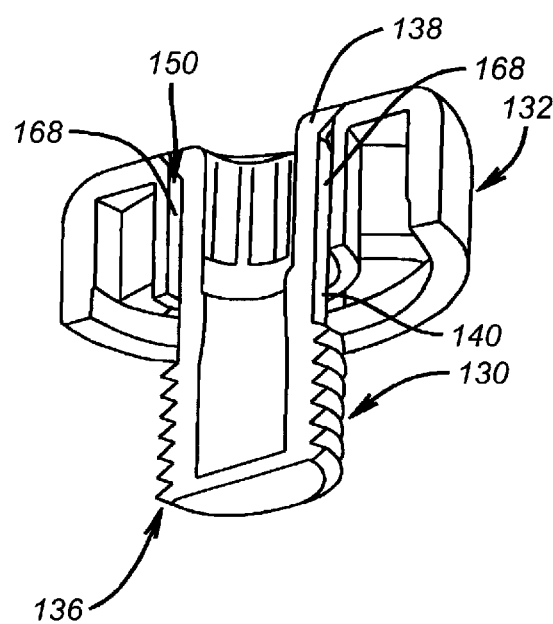
FIG. 5B is a cross sectional view of FIG. 5A after the collar and the shaft are connected.

The shaft and the collar may be connected together in other ways known to those skilled in the art. FIGS. 5A and 5B show an example of an alternate way to connect these two components. Here, the external threads of the shaft 130 have an outer diameter that is less than the diameter of the central opening 150 of the collar 132. The lip 138, however, has a diameter that is greater than that of the central opening. As such, the distal end 136 passes through the central opening until the lip abuts against the top of the collar. As shown in FIG. 5B, a small gap 168 is left between the central opening of the collar and the smooth body portion 140 of the shaft.

Turning back to FIGS. 2 and 3, driving tool 106 is designed to engage the healing screw in order to drive the dental implant into the jawbone of a patient at an implantation site. The driving tool has an elongated cylindrical configuration and extends from a proximal end 180 to a distal end 182. The proximal end connects to a dental wrench (not shown), such as an electric or motorized dental driving tool. The proximal end may have any one of various configurations known to those skilled in the art for connecting to a dental driving tool. In the preferred embodiment, the proximal end has a right angle latch end as shown in FIGS. 2 and 3. The distal end has an engagement feature 184 for connecting to and engaging with the healing screw. Engagement feature 184 includes a cylindrical base or platform 185 and a plurality of male projections 186 disposed in a generally circular pattern. The male projections extend downwardly from an end surface 188 of the platform 185. The male projections are sized to create a frictional engagement with engaging region 152. The engagement feature 184 also includes a central engaging member 190 extending downwardly and centrally from the distal end. The central engaging member 190 is sized to fit into the axial bore 142 of the shaft 130, while the male projections 186 engage engaging region 152. The central engaging member 190 is preferably longer than the male projections 186. This allows the central engaging member 190 to enter the axial bore 142 prior to the engagement of the male projections 186 with the engaging region 152. The central engaging member 190 assists the user in aligning the axis of the driving tool 106 with the axis of the healing screw 104. As shown in FIGS. 2, 3, 6A, and 6B groove 183 reduces the probability of breakage of the male projections 186 due to the application of excessive torque loads to driver tool 106. Groove 183 is sized to be the weakest point of driver tool 106. If an excessive torque load is applied to driver tool 106, it will fail at groove 183. Advantageously, this will leave only two broken pieces of driver tool 106.

Figure 6A:
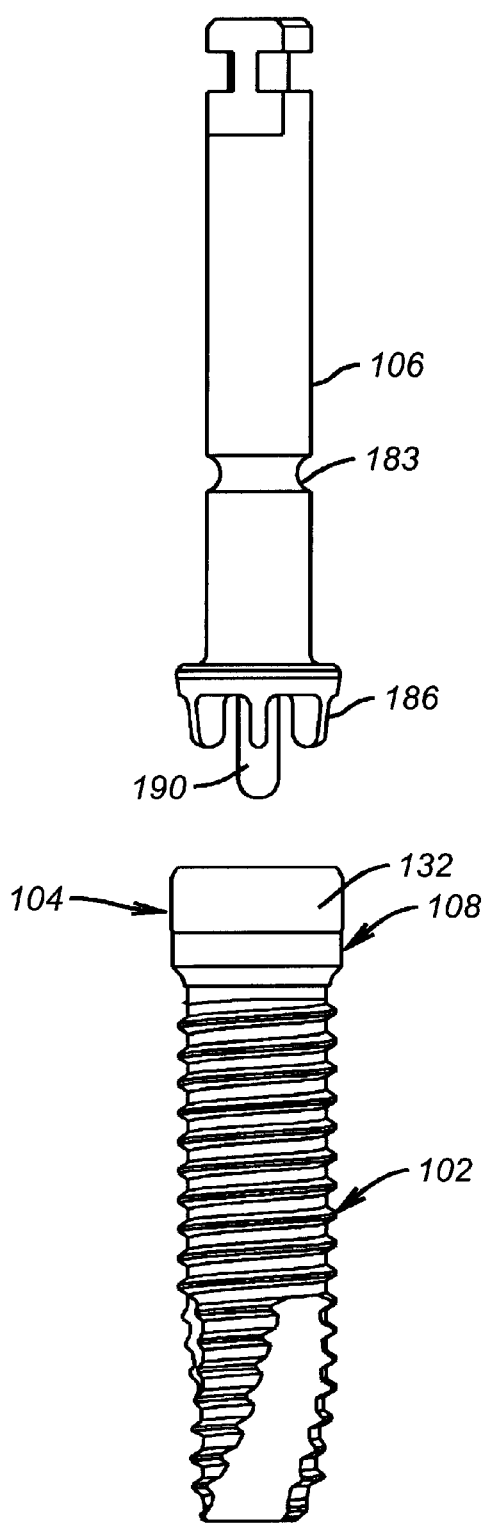
FIG. 6A is a plan view of the driving tool with the healing screw connected to the dental implant.
Figure 6B:
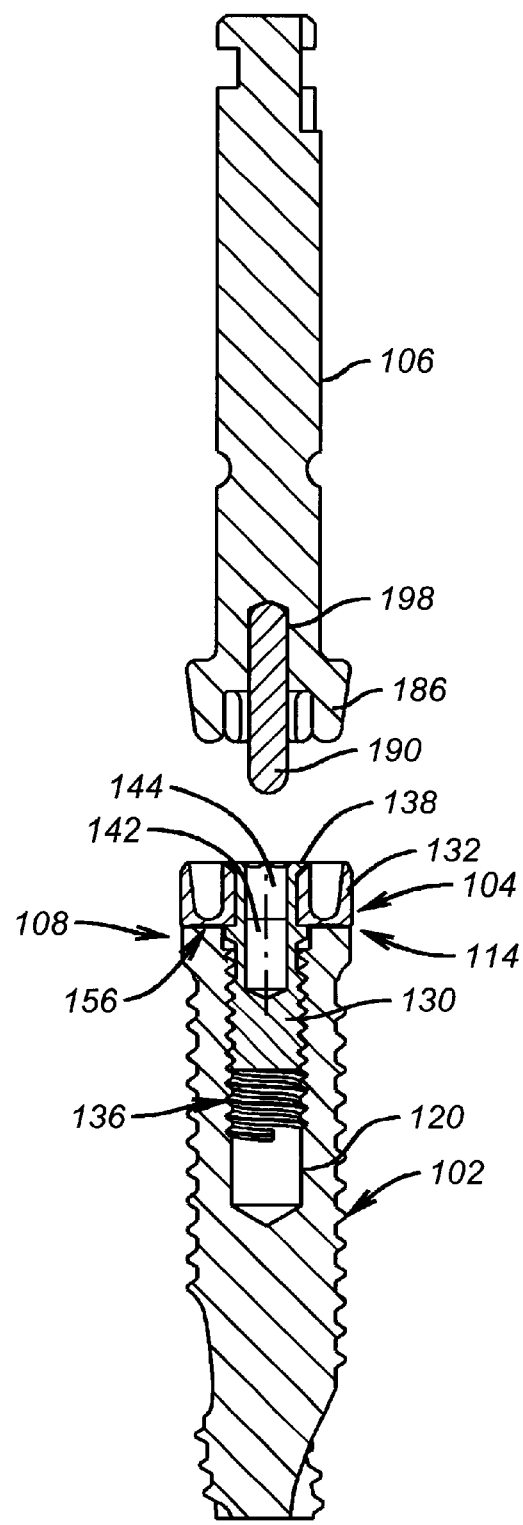
FIG. 6B is a cross sectional view of FIG. 6A.

As shown in FIGS. 6A and 6B, the healing screw 104 attaches to the coronal end 108 of the dental implant 102. The healing screw may be attached to the dental implant during assembly and thereafter packaged and shipped as a single unit. As such, during the implantation procedure, no steps are required to attach a healing cap to the dental implant.

As best seen in FIG. 6B, the shaft 130 of the healing screw threads into the threaded axial bore 120 of the implant. The lip 138 of the shaft presses against the collar 132 to retain the healing screw to the implant. A dental driving tool may be inserted into the axial bore 142 to engage the engaging surface 144 to tighten and loosen the healing screw.

One important advantage of the present invention is that the shaft 130 and the collar 132 may rotate relative to one another once they are connected together. This rotation enables the healing screw to be placed on and engaged with the end of the implant. Looking to FIGS. 2–6, during installation of the healing screw to the implant, the threaded distal end 136 of the shaft 130 is threaded into the axial bore 120 of the implant. The engaging region 156 of the collar 132 is positioned to engage the engaging feature 114 of the implant. Even while the collar is engaged with the end of the implant, the shaft may be rotated until the healing screw is securely and tightly fastened to the implant.

In order to remove the healing screw, the shaft is unscrewed and pulled away from the implant. As the shaft is initially loosened, the collar does not rotate, but remains engaged with the engaging feature 114 of the implant; the collar moves in an axial direction only until the engaging region 156 has cleared the implant engaging feature 114. As the shaft is being pulled away from the implant, the shoulder 164 (shown best in FIG. 4B) pushes and lifts the collar. As such, the healing screw is removed as a single unit.

Preferably, the shaft and the collar may be removed as a single unit when the healing screw is disengaged and removed from the implant. Various ways known to those skilled in the art may be employed to enable the shaft and the collar to be removed in this fashion. For example, the collar may be snugly fit against the shaft. As the shaft is lifted off the implant, friction will enable the collar to lift off too. As another example, the central opening of the collar may be threaded. The threaded distal end of the shaft could thread through the threads on the collar to position the healing screw on the implant. Then, as the shaft is being removed from the implant, the threaded distal end enables the collar to be lifted off the implant.

FIG. 6B illustrates a cross sectional view of the driving tool 106. As shown, some of the male projections 186 are integrally formed as part of the driving tool. The central engaging member 190 consists of a separate member having an elongated cylindrical configuration. The distal end of the driving tool has a cylindrical bore 198 for receiving the central engaging member. Preferably, this engaging member is permanently press fit into the bore. In another embodiment (not shown), the central engaging member may be integrally formed as part of the driving tool.

Figures 7A, 7B:
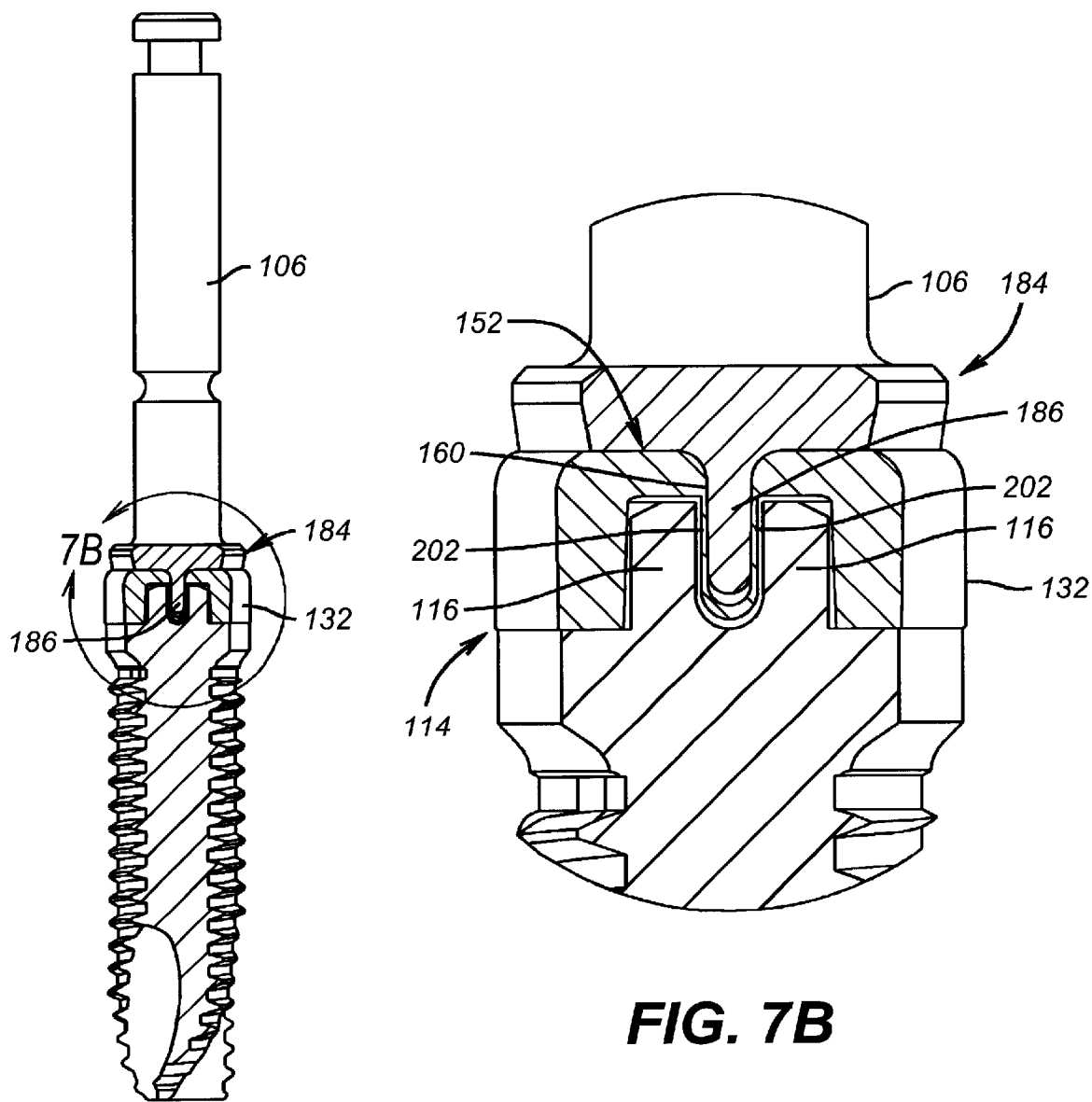
FIG. 7A is a partial cross sectional plan view of the driving tool and the healing screw both connected to the dental implant.
FIG. 7B is an enlarged partial cross sectional view of FIG. 7A taken along line 7B.

FIGS. 7A and 7B show the driving tool 106 connected to the implant and healing screw shown and described in FIGS. 6A and 6B. The engagement feature 184 of the driving tool is connected to and engaged with the engaging region 152 of collar 132. As shown, the male projections 186 are disposed in cavities or recesses 160. In this position, the central engaging member 190 (FIG. 6B) is disposed in the axial bore 142 (FIG. 6B) of the shaft 130.

FIGS. 7A and 7B also show that the male projections 186 of the engagement feature 184 interdigitate with the male tines 116 of the implant 102. This illustrates an important means by which the healing screw achieves its compact and advantageous size. Namely, the engaging features of the driver tool 106, and the engaging features of the implant 102 both intersect a common plane that is perpendicular to the axis of the implant.

One advantage of the preferred embodiment of the present invention is that driving tool imparts a driving force substantially directly to the implant. As best seen in FIG. 7B, the male projections 186 extend between the male tines 116. A thin wall 202 of the collar is located between the male projections and the male tines. As such, the driving force or torque from the engagement feature 184 of the driving tool imparts substantially directly to the engaging feature 114 of the implant, with the thin wall 202 experiencing only a substantially compressive force.

Figure 8:
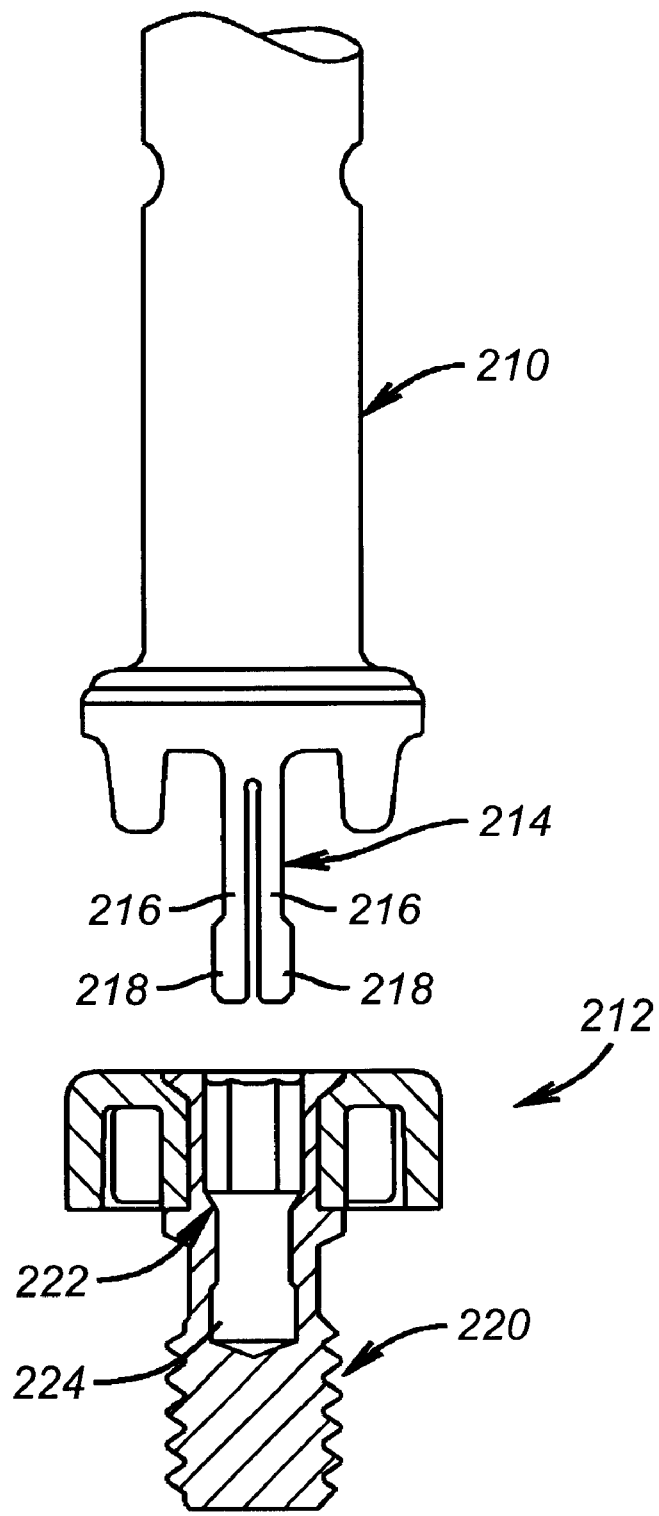
FIG. 8 is an alternate embodiment of the driver tool and healing screw.

Turning now to FIG. 8, an alternate embodiment of the driver tool 210 and healing screw 212 are shown. Here, the central engaging member 214 has two resilient legs 216 separated by a space. The legs extend downwardly and have an expanded or enlarged portion 218 at the distal tip.

The healing screw in FIG. 8 is similar to the one described in connection with FIGS. 4A–4E, but for one exception. The shaft 220 has an axial bore 222 that has a cylindrical configuration with an enlarged area 224 at the distal end. This enlarged area is sized to receive the enlarged portion 218 of the central engaging member 214.

While the central engaging member is being inserted into the axial bore of the shaft, the legs 216 initially compress together. The legs stay compressed until the enlarged head portion 218 is positioned into the enlarged area 224 of the shaft; at which time the legs decompress and expand back to their original position. In this position, the driver mount is able to carry or hold the healing screw and dental implant, if one is connected. The central engaging member of the driving tool may be removed from the axial bore of the shaft if a small separation force is applied. The separation force should be sufficient so the driver tool can hold the healing screw and dental implant and carry them to the implantation site without the driver tool inadvertently separating from the healing screw.

Figure 9:
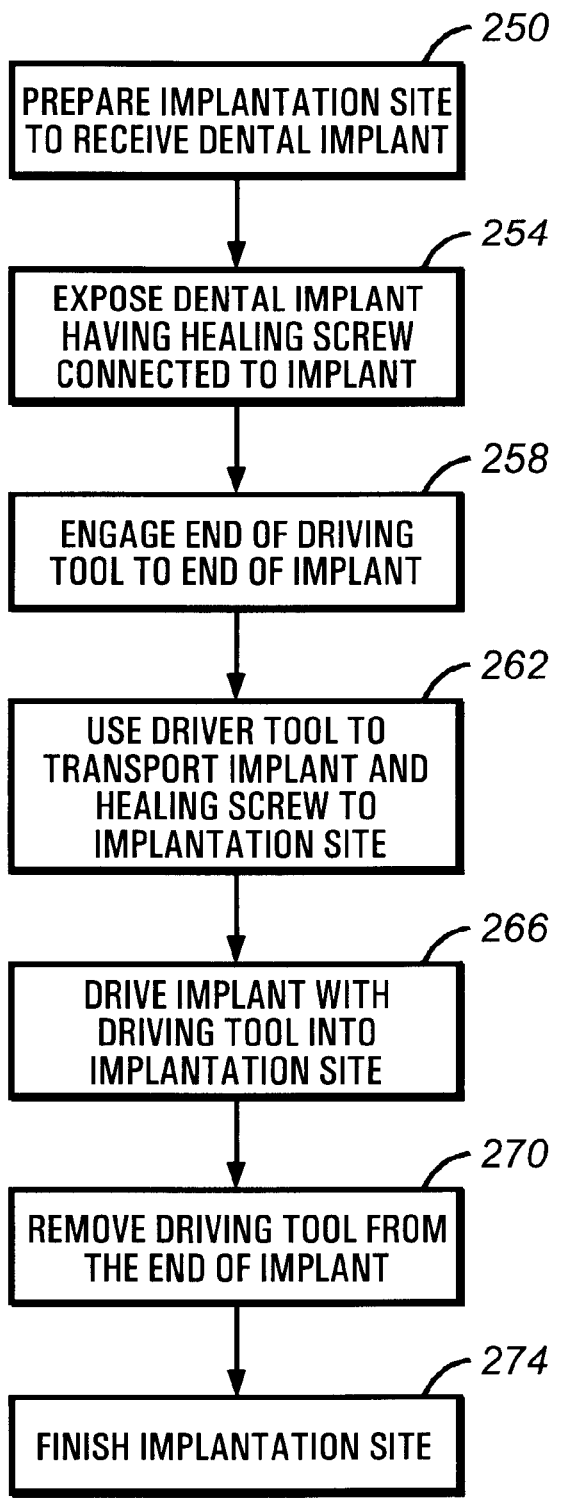
FIG. 9 shows a block diagram illustrating the method of the present invention.

FIG. 9 shows a block diagram of the preferred method of the present invention. The diagram teaches a method to surgically implant a single dental implant, but variations to this method may be used for other dental implantation procedures, such as multiple teeth restorations or single stage restorations. In block 250, the implantation site is prepared to receive the dental implant. Preparation of the site may be performed in a conventional manner known to those skilled in the art. Typically, the gingival tissue of the patient is cut, and the jawbone is exposed. Then, a hole is drilled into the jawbone.

Next, as shown in block 254, the dental implant is exposed. Dental implants are shipped in sterile, protective packages, including for example, plastic vials or plastic bubble-like containers. The package is opened once the implant is ready for use during the surgical implantation procedure. In the preferred embodiment, the healing screw and implant are connected together and packaged together, as shown and discussed in connection with FIGS. 6A and 6B.

In block 258, the distal end of the driving tool is engaged with the implant. Here, the engagement feature of the driving tool connects to and engages with the engaging region of the healing screw and the coronal end of the implant, as shown in FIGS. 7A and 7B.

In block 262, the driving tool transports or carries the implant and healing screw to the implantation site. The driving tool is then positioned so the distal end of the implant is over the bore in the jawbone.

As shown in block 266, the driving tool drives the implant into the implantation site. Typically, the driving tool is an electric, motorized dental wrench. Once the implant is driven to the desired location, the end of the driving tool is removed from the implant and healing screw, as shown in block 270. Per block 274, the implantation site is then completed in a conventional manner known to those skilled in the art.

Figure 10:
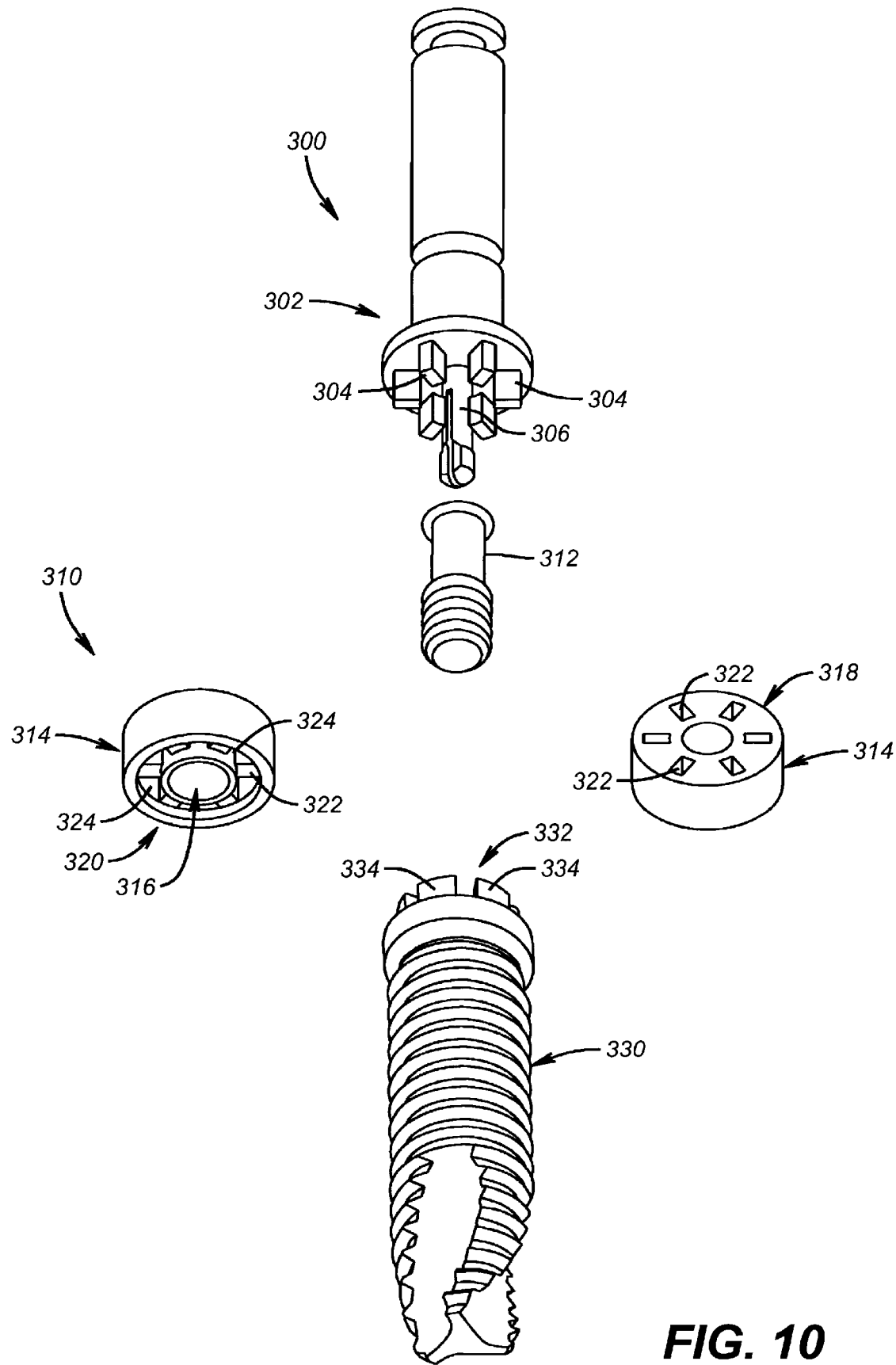
FIG. 10 is an exploded view of an alternate embodiment showing perspective top and bottom views of the collar.

FIG. 10 shows an alternate embodiment of the present invention. Here, the driving tool 300 has an engagement feature 302 with a plurality of male protrusions 304. These protrusions have a rectangular configuration. The central engaging member 306 has a configuration similar to the one described in connection with FIG. 8.

Looking now to the healing screw 310, the shaft 312 has a configuration similar to the one described in connection with FIG. 8. The collar 314 (shown in two different perspective views) has central opening 316 extending through its body, a first engaging region 318, and a second engaging region 320. Engaging region 318 engages the engagement feature 302 of the driving tool 300 and has a plurality of rectangular cavities or recesses 322. Each cavity receives a corresponding male protrusion 304.

Engaging region 320 consists of a plurality of cavities or recesses 324 formed between adjacent rectangular cavities 322. These cavities 324 extend circumferentially around the collar.

Implant 330 has an engaging feature 332 that consists of a plurality of male tines 334. These tines fit into cavities 324 of engaging region 320. Further, the tines 334 are spaced apart to receive the male protrusions 304 of the driving tool.

FIGS. 11 through 12 show an alternate dental implant delivery system 400. The delivery system generally includes a dental implant 402, a healing screw 404, and a driving tool 406. This delivery system 400 has some similarities and differences with the delivery system 100 of FIGS. 2 and 3. Differences between the two delivery systems are noted below.

The implant 402 has a coronal end with an engaging feature 408 having a polygonal projection 410. This polygon is shown as a hexagon. The coronal end also includes a threaded axial bore 412 extending downwardly into the body of the implant.

Although the engaging feature is shown as a hexagon, other configurations known to those skilled in art (such as an octagon or star) may be used as well. Further, although the implant is shown with a male polygonal projection at the coronal end, a female polygonal recess is also within the scope of this invention. Corresponding changes, of course, would have to be made to the healing screw 404 and driving tool 406 to properly engage with and connect to an implant with such a polygonal recess.

Figure 13A:
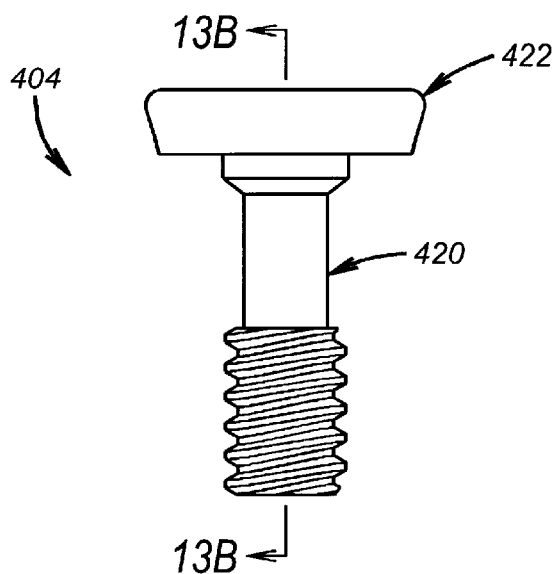
FIG. 13A is a plan view of the healing screw of FIG. 11A.
Figure 13B:
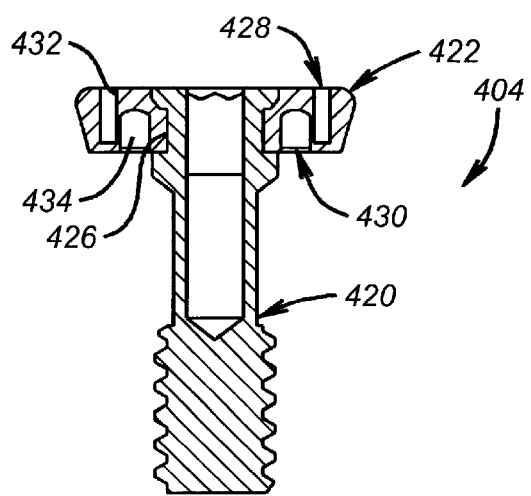
FIG. 13B is a cross sectional view taken along line 13B of FIG. 13A.

Looking also to FIGS. 13A and 13B, healing screw 404 consists of two separate and distinct components: a shaft 420 and a collar 422. The shaft has a configuration similar to the shaft 104 shown in FIG. 4B. The collar has a ring or cylindrical shape with a central opening 426 extending through its body. The collar has two engaging regions. One engaging region 428 is located at a proximal end; and another engaging region 430 is located at a distal end. Engaging region 428 is designed to engage the end of driving tool 406 and has a male polygonal projection 432. Preferably, this projection is a hexagon. Engaging region 430 is designed to engage the engaging feature 408 of implant 402 and has a polygonal recess 434 shaped as a hexagon. This recess 434 receives and engages the hexagonal projection 410 of the implant.

The driving tool has an elongated cylindrical configuration and extends from a proximal end 440 to a distal end 442. The proximal end has a configuration similar to the driving tool 106 described in connection with FIGS. 2 and 3. The distal end 442 has an engagement feature 446 for connecting to and engaging with the engaging region 428 of collar 422. Engagement feature 446 includes a cylindrical base or platform 448, a cylindrical wall 450 extending from this base, and a female polygonal recess 450 formed within this wall. This recess is shown as a hexagon and should have a size and configuration to connect and engage with polygonal projection 432 of collar. 422. Further, the recess 450 and projection 432 may frictionally engage one another to enable the driving tool to carry or transport the healing screw while it is connected to the implant.

The present invention has numerous advantages. As described in connection with FIG. 9, only a few steps are required to place a dental implant into a patient's jawbone during a dental implantation procedure. The healing screw is pre-assembled to the implant by the manufacturer during packaging, so no steps are necessary to attach it to the implant. Further, the healing screw functions both to drive the implant (like a conventional driver mount) and to protect the coronal end of the implant (like a conventional healing cap). As such, no steps are necessary during the implantation procedure to attach or separate a driver mount or healing cap.

As another advantage, the number of tools required to place the dental implant is minimized. As discussed in FIG. 9, the driving tool of the present invention serves multiple functions. The tool can connect to the healing screw and transport it and the implant to the implantation site. Further, the tool serves to drive the implant into the jawbone. As such, separate tools are not required to transport the implant or healing screw to the implantation site, connect or disconnect a driver mount to the implant, or drive the implant.

As another advantage, the risk of contaminating the coronal end of the implant (including the axial bore) is reduced. The healing screw seals the internal axial bore of the implant and helps prevent contaminants (including bacteria) from entering the axial bore during the implantation procedure and during the osseointegration period (a time period, usually 3-6 months, extending from the time the implant is implanted until a second surgical procedure when the permanent prosthesis is connected to the implant). In this regard, the implant is packaged and shipped with the healing screw attached. As such, the implant can be carried to the implantation site, driven into the jawbone, and left on the implant during the osseointegration period without the healing screw ever being removed. The axial bore of the implant is thus never directly uncovered during the implantation procedure.

As another advantage, the view of the anti-rotational feature on the end of the implant is not occluded during the implantation procedure. Looking to FIGS. 4D, 3, and 11B, the proximal end of the collar has a shape that reveals the orientation of the anti-rotational feature of the implant. While the healing screw is positioned on the end of the implant, the orientation of the anti-rotational features is visible. As such, the dentist or oral surgeon can view the orientation of the anti-rotational features even once the implant is positioned into the jawbone of the patient.

The present invention has numerous other advantages as well. Some of these advantages are more fully articulated in the Summary section, while others are apparent from the description of the figures.

What is claimed is:

1. A dental implant system, comprising:
   a dental implant having a coronal end with an engaging feature and a threaded internal bore;
   a healing screw having two separate and distinct components, including a shaft and a collar;
   the shaft having an elongated cylindrical configuration, a proximal end with an engaging feature, a smooth outer surface portion, a distal end with external threads, a lip that extends around the proximal end of the shaft and a shoulder;
   the collar having a cylindrical shape with a central opening extending through the collar, a proximal end with a first engaging region, and a distal end with a second engaging region: and
   wherein the distal end of the shaft extends through the central opening of the collar, the collar is connected to the smooth outer surface portion of the shaft, the shaft rotates within the central opening while the second engaging region of the collar remains engaged with the engaging feature of the implant, the lip abuts against the proximal end of the collar, and the shoulder abuts against the distal end of the collar.

2. The dental implant system of claim 1 in which the smooth outer surface portion extends between the shoulder and the lip.

3. The dental implant system of claim 1 in which the shoulder and the lip retain the collar around the shaft.

4. The dental implant system of claim 1 in which the shaft rotates within the central opening while the external threads of the shaft thread into the threaded internal bore of the implant.

5. The dental implant system of claim 1 in which the engaging feature of the implant is a male hexagonal projection, and the second engaging region of the collar is a female hexagonal recess that engages the male hexagonal projection.

6. The dental implant system of claim 1 in which the engaging feature of the implant is a plurality of male tine projections, and the second engaging region of the collar is a plurality of recesses that engage the male tine projections.

7. The dental implant system of claim 1 in which the shaft is made of titanium and the collar is made from a polymer.

8. The dental implant system of claim 1 in which the collar is injection molded around the shaft.

9. The dental implant system of claim 1 in which the engaging feature of the shaft includes a multi-sided recess.

10. The dental implant system of claim 9 in which the multi-sided recess, has a hexagonal shape.

11. The dental implant system of claim 1 in which the external threads of the shaft have a diameter that is smaller than the diameter of the central opening of the collar.

12. The dental implant system of claim 1 in which the second engaging region of the collar engages the engaging feature of the implant while the implant is driven into a jawbone.

13. The dental implant system of claim 12 in which the second engaging region transfers torque to the engaging feature.

14. The dental implant system of claim 1 in which the healing screw seals the internal bore of the implant.

15. A method for implanting a self-tapping dental implant and a dental healing screw into a jawbone of a patient, comprising the steps of:
providing the dental implant with a coronal end having an engaging feature and a threaded axial bore;
providing the healing screw with a shaft and a collar, the collar having a first engaging region at a proximal end and a second engaging region at a distal end and a central opening, the shaft extending through the central opening and having an external threads;
providing a dental driving tool having a distal end with an engagement feature;
engaging the second engaging region of the collar with the engaging feature of the implant;
rotating the shaft to threadably engage the external threads with the threaded axial bore of the implant;
cutting gingival tissue of the patient to expose the jawbone;
forming a hole into the jawbone;
engaging the engagement feature of the driving tool with the first engaging region of the collar;
transporting the implant and healing screw connected to the driving tool to the jawbone;
positioning a distal end of the implant into the hole;
driving the implant with the driving tool into the hole until the implant is fully seated in the hole;
removing the engagement feature of the driving tool from the first engaging region of the collar; and
covering the implant and healing screw with the gingival tissue.

16. A method for connecting a dental healing screw to a dental implant, comprising the steps of:
providing the dental implant with a coronal end having an engaging feature and a threaded axial bore;
providing the healing screw with a shaft made of titanium and a collar made of polymer, the collar having a engaging region at a distal end and a central opening, the shaft extending through the central opening and having an external threads;
engaging the engaging region of the collar with the engaging feature of the Implant; and
rotating the shaft within the central opening to threadably engage the external threads of the shaft with the threaded axial bore of the implant.

17. The method of claim 16 further comprising the steps of:
providing a dental tool with having a distal end with an engagement feature;
providing the shaft including a proximal end with an axial bore having a tool engaging surface;
engaging the engagement feature with the tool engaging surface; and rotating the dental tool to perform the step of rotating the shaft within the central opening.

18. A method for implanting a self-tapping dental implant and a dental healing screw into a jawbone of a patient, comprising the steps of:
providing the dental implant with a coronal end having an engaging feature and a threaded axial bore;
providing the healing screw with a shaft and a collar, the collar having a first engaging region at a proximal end and a second engaging region at a distal end and a central opening, the shaft extending through the central opening and having an external threads;
providing a dental driving tool having a distal end with an engagement feature;
connecting the healing screw to the implant with the second engaging region of the collar directly engaged with the engaging feature of the implant;
cutting gingivial tissue of the patient to expose the jawbone;
forming a hole into the jawbone;
engaging the engagement feature of the driving tool directly with the first engaging region of the collar;
positioning a distal end of the implant at the hole;
driving the implant with the driving tool into the hole until the implant is fully seated in the hole;
removing the engagement feature of the driving tool from the first engaging region of the collar; and
covering the implant and healing screw with the gingival tissue.

19. A method for implanting a dental implant and a dental healing screw into a jawbone of a patient, comprising the steps of:
providing the dental implant with a coronal end having an axial bore;
providing the healing screw with a metallic shaft and a polymeric collar, the collar having an engaging region at a proximal end and a central opening, the shaft extending through the central opening;

providing a dental driving tool having a distal end with an engagement feature;

connecting the healing screw to the coronal end of the implant to seal the axial bore of the implant;

cutting gingivial tissue of the patient to expose the jawbone;

forming a hole into the jawbone;

engaging the engagement feature of the driving tool directly with the engaging region of the collar;

driving the implant with the driving tool into the hole;

removing the engagement feature of the driving tool from the engaging region of the collar; and covering the implant and healing screw with the gingival tissue 20. A method for implanting a self-tapping dental implant and a dental healing screw into a jawbone of a patient, comprising the steps of:

providing the dental implant with a coronal end connected to and engaged with the healing screw, the healing screw having a proximal end with an engaging region;

providing a dental driving tool having a distal end with an engagement feature;

drilling a hole into the jawbone of the patient;

connecting the engagement feature of the driving tool directly with the engaging region of the healing screw;

transporting the implant, healing screw, and driving tool to the jawbone;

driving the implant into the hole with the driving tool until the implant is fully seated in the hole; and removing the engagement feature of the driving tool from the engaging region of the healing screw.

21. A dental implant system, comprising:

a dental implant having a coronal end with an engaging feature and a threaded internal bore;

a healing screw having two separate and distinct components, including a shaft made of titanium and a collar made of polymer;

the shaft having an elongated cylindrical configuration, a proximal end with an engaging feature, a smooth outer surface portion, and a distal end with external threads;

the collar having a cylindrical shape with a central opening extending through the collar, a proximal end with a first engaging region, and a distal end with a second engaging region; and wherein the distal end of the shaft extends through the central opening of the collar, the collar is connected to the smooth outer surface portion of the shaft, the shaft rotates within the central opening while the second engaging region of the collar remains engaged with the engaging feature of the implant.

22. The dental implant system of claim 21 in which the second engaging region of the collar engages the engaging feature of the implant to fully seat and drive the implant into a jawbone.

23. The dental implant system of claim 22 in which the second engaging region transfers torque directly to the engaging feature.

24. The dental implant system of claim 21 in which the healing screw seals the internal bore of the implant.

* * * * *